United States Patent
Coupland et al.

(10) Patent No.: US 6,340,485 B1
(45) Date of Patent: Jan. 22, 2002

(54) COMPOSITIONS AND USES THEREOF

(75) Inventors: Keith Coupland, Hotham; Claire Elizabeth Packer, Bessacarr, both of (GB)

(73) Assignee: Croda International PLC, North Humberside (GB)

( * ) Notice: Subject to any disclaimer, the term of this patent is extended or adjusted under 35 U.S.C. 154(b) by 0 days.

(21) Appl. No.: 09/523,731

(22) Filed: Mar. 13, 2000

Related U.S. Application Data

(63) Continuation-in-part of application No. 09/308,927, filed on May 27, 1999, now abandoned, which is a continuation-in-part of application No. 09/308,928, filed on May 27, 1999, now abandoned.

(30) Foreign Application Priority Data

| Jun. 3, 1996 | (GB) | 9611529 |
| Jun. 3, 1996 | (GB) | 9611530 |
| Jun. 3, 1996 | (GB) | 9611531 |

(51) Int. Cl.$^7$ .................. A61K 35/78; A61K 31/20; A01N 37/00; A01N 37/12
(52) U.S. Cl. .................. 424/776; 514/558; 514/560
(58) Field of Search .................. 424/195.1, 401, 424/776; 514/558, 560

(56) References Cited

U.S. PATENT DOCUMENTS

| 3,405,151 A | * | 10/1968 | Pike | 554/184 |
| 4,386,072 A | * | 5/1983 | Horrobin | 424/722 |
| 4,444,755 A | * | 4/1984 | Horrobin | 424/642 |
| 4,977,187 A | * | 12/1990 | Horrobin | 514/560 |
| 5,120,760 A | * | 6/1992 | Horrobin | 514/458 |
| 5,158,975 A | * | 10/1992 | Guichardant et al. | 514/560 |
| 5,178,873 A | * | 1/1993 | Horrobin et al. | 424/422 |
| 5,196,198 A | * | 3/1993 | Shaw et al. | |
| 5,223,285 A | * | 6/1993 | DeMichele et al. | 426/72 |
| 5,310,556 A | * | 5/1994 | Ziegler | 424/401 |
| 5,643,583 A | * | 7/1997 | Voultoury et al. | 424/401 |
| 5,690,947 A | * | 11/1997 | Habif et al. | 424/401 |
| 5,855,893 A | * | 1/1999 | Weinkauf et al. | |

FOREIGN PATENT DOCUMENTS

| EP | 0399417 | | 11/1990 |
| EP | 0421867 | * | 4/1991 |
| EP | 0430870 | | 6/1991 |
| EP | 0454102 | * | 10/1991 |
| EP | 0460848 | | 12/1991 |
| EP | 0457950 | | 10/1992 |
| EP | 0711503 | | 5/1996 |
| FR | 2648347 | | 6/1989 |
| FR | 2679109 | * | 1/1993 |
| GB | 2118567 | | 11/1983 |
| WO | 9415464 | | 7/1994 |

OTHER PUBLICATIONS

Smith et al. J. Am. Oil Chemist's Soc. vol. 41, No. 4, pp. 290–291, 1964.*
Siddiqui et al. J. Oil Technol. Assoc. India. vol. 5, No. 1, pp. 8–9, abstract enclosed, 1973.*

* cited by examiner

*Primary Examiner*—Christopher R. Tate
(74) *Attorney, Agent, or Firm*—Stevens, Davis, Miller & Mosher, L.L.P.

(57) ABSTRACT

A composition comprising in the range of from 1 to 20% by weight of the total composition of an oil extracted from the seeds of Borignaceae, particularly E, plantagineum, has particular advantages over oils extracted from other seeds. The oil comprises in the range of from 5 to at least 20% stearidonic acid triglyceride and 80 or less to 95% other fatty acid triglycerides, by weight of the total fatty acids in the oil extract, which stearidonic acid or other fatty acid(s) may optionally have been converted to a derivative thereof, and optionally a physiologically acceptable carrier therefor. The compositions are particularly suited for oral or topical administration and are for dietary, cosmetic, pharmaceutical and healthcare use.

32 Claims, No Drawings

COMPOSITIONS AND USES THEREOF

CROSS-REFERENCE TO RELATED APPLICATIONS

This application is a continuation-in-part of U.S. Ser. No. 09/308,927, filed May 27, 1999, now abandoned and 09/308,928, filed May 27, 1999, now abandoned the entire disclosures of which are herein incorporated by reference.

BACKGROUND OF THE INVENTION

1. Field of the Invention

This invention relates to the use of oils containing triglycerides of essential fatty acids for inter alia topical and dietetic purposes, and to compositions comprising such oils.

2. Description of the Related Art

Triesters of glycerol are known as triglycerides or triacylglycerols. If the triglyceride is solid at room temperature, then it is generally considered to be a fat, whereas if it is liquid at room temperature, then it is generally considered to be an oil. Most triglycerides in animals are fats, while most triglycerides in vegetables tend to be oils. Fatty acids can be obtained from these fats or oils by hydrolysis. Certain fatty acids, called essential fatty acids, must be present in the human diet and are used in the body to synthesize, for example, prostaglandins. There are two main series of essential fatty acids: one is called the 3n family (also known as the z-3 family); and the other is called the n6 family (also known as the z-6 family).

Stearidonic acid (SA) is a polyunsaturated fatty acid of the n3 family; it is an essential fatty acid. Chemically, it can be described as 6c,9c,12c,15c-octadecatetraenoic acid or 18:4n3. Other essential fatty acids are linoleic acid (LA), a-linolenic acid (ALA) and c-linolenic acid (GLA)—these acids can be described as C18:2n6, C18:3n3 and C18:3n6, respectively. Stearidonic acid is found in marine oils, some plant oils and in lipids isolated from micro-organisms. It is also produced in the human body by the desaturation of a-linolenic acid (1 8:3n3) with the enzyme <–6 desaturase. The metabolic transformation in the human body of n3 fatty acids by desaturation and elongation takes place as follows:

|  | 18:3 a-linolenic acid |
|---|---|
| <6 desaturase | |
|  | 18:4 stearidonc acid |
| elongase | |
|  | 20:4 eicosatetraenoic acid |
| <5 desaturase | |
|  | 20:5 eicosapentaenoic acid |
| elongase | |
|  | 22:5 docosapentaenoic acid |
| <4 desaturase | |
|  | 22:6 docosahexaenoic acid |

The activity of the enzyme <6 desaturase is known to be of lower activity following certain illnesses, and in old age; its activity can also be lowered by poor diet and certain lifestyles. This is significant, because if the activity of <6 desaturase is lowered, then the body's capacity to make stearidonic acid (and the other compounds in the scheme shown above) is also lowered. One way to remedy this problem is to take a dietary supplement containing stearidonic acid.

It is known that the oils of the pips of certain fruits contain triglycerides of a number of fatty acids. In GB-A-2118567, it is disclosed that an oil extracted from the pips of the fruit of blackcurrants, redcurrants and gooseberries contain triglycerides of fatty acids in the proportions shown in Table 1.

TABLE 1

| Fatty Acid | Blackcurrants wt % | Redcurrants wt % | Gooseberries wt % |
|---|---|---|---|
| C16:0 | 6–7 | 4–5 | 7–8 |
| C18:0 | 1–2 | 1–2 | 1–2 |
| C18:1 cis | 9–10 | 14–15 | 15–16 |
| C18:1 trans | 0.5 | 0.5–1 | 1–2 |
| C18:2n6 | 47–49 | 41–42 | 29–41 |
| C18:3n6 | 15–19 | 4–5 | 10–12 |
| C18:3n3 | 12–14 | 29–31 | 19–20 |
| C18:4n3 | 3–4 | 2.5–3.5 | 4–5 |

However, none of the materials in Table 1 is very useful as a source of stearidonic acid, because this acid is present in such a low concentration. In order to use these materials as a source of stearidonic acid, it would be necessary either to use them in large quantities or to carry out expensive chemical processing to concentrate the stearidonic acid. Accordingly, there is a need for a material that is rich in stearidonic acid but that does not contain any toxic compounds.

SUMMARY OF THE INVENTION

A rich natural, non-toxic, source of stearidonic acid that can be used to make a wide range of dietetic, cosmetic, personal care and healthcare products is found in the oil of seeds of the Borignaceae family. However, we have surprisingly found that the oil itself can be used in dietetic, cosmetic, personal care and healthcare products, without the need for additional treatment or purification, and having advantages over the purified stearidonic acid.

In one aspect, the invention provides the use of an oil extracted from seeds of the Borignaceae family in topical application to, or oral ingestion by, the human or animal body. This oil alone may be used for these purposes or, preferably, it is used to form a part of a composition e.g. for topical application to, or oral ingestion by, the human or animal body.

DETAILED DESCRIPTION OF THE PREFERRED EMBODIMENTS

In an especially advantageous embodiment, the seeds are of the genus Echium; in particular, we have found that the seeds of *Echium vulgaris* and *Echium plantagineum* are very useful, especially *E. plantagineum*.

Oil extracted from the seeds of the Borignaceae family contains the triglyceride of stearidonic acid. This is described in greater detail in our co-pending U.S. patent application Ser. No. 09/308,928, filed May 27, 1999, which is a 35 USC §371 National Stage of PCT patent application filed Jun. 3, 1997, entitled "Vegetable Oil Composition" (PCT/GB97/01497), the entire disclosure of which is herein incorporated by reference.

In general, the oil contains stearidonic acid (in the form of the triglyceride) in an amount greater than 5wt %, preferably greater than 5.5wt %, more preferably greater than 10wt %, and most preferably greater than 15wt %; the oil may contain as much as 20wt % stearidonic acid, or more. The oil can be obtained at these concentrations without carrying out any purification process to increase the concentration of stearidonic acid in the oil. The compositions of three oils obtained from the seeds of the Borignaceae family have been analysed, and found to have fatty acids present (in the form of triglycerides) in the amounts shown in Table 2.

TABLE 2

| Fatty Acid | E. vulgaris wt % | E. Plantagineum wt % | Trichodesma Zeylanicum wt % |
|---|---|---|---|
| 16:0 | 6.2 | 7.6 | 9.4 |
| 18:0 | 2.0 | 3.8 | 5.8 |
| 18:1 | 8.0 | 16.7 | 26.8 |
| 18:2 (LA) | 10:3 | 16 | 18.2 |
| 18:3 (GLA) | 5.3 | 11.9 | 5.5 |
| 18:3 (ALA) | 47.3 | 29.9 | 26.8 |
| 18:4 (SA) | 19.8 | 12.3 | 5.7 |
| Other | 1.1 | 1.8 | 1.8 |

Moreover, we have surprisingly found that these oils are especially advantageous in their ability to inhibit UVB-induced release of $PGE_2$: Ultraviolet (UV) light in the wavelength range of 290nm to 340 nm is covered by the range UVB (290nm to 320nm) and UVA2 (320nm to 340nm); UV light in this range is erythemognic. Exposure to small amount of UVB can be beneficial, since it is required for synthesis of vitamin D in the skin. However, larger amounts of UV radiation cause sunburn, which is characterised by erythema, pain swelling and blistering; in extreme cases there is epidermal necrosis.

Sunburn is a classical cutaneous inflammation whose pathogenesis is not completely understood. The release of inflammatory mediators including eicosanoids and cytokines seems to be important. UVB exposure can also compromise the immune system. Chronic UV exposure results in accelerated skin aging called photo-aging; it can also lead to the development of skin cancer. The major target in UV-induced carcinogenesis is probably DNA. However, the suppressed immune system could play an important role in the pathogenesis of these neoplasms. In addition to necrosis induced by UV exposure, there is evidence that even acute exposure can result in apoptosis (programmed cell death) of affected keratinocytes.

Cutaneous inflammation caused by UVB is mediated by various cytokines such as tumour necrosis factor-alpha (TNFa) and interleukin 1a (IL1a). In addition, UVB induces the release of arachidonic acid from cell membrane phospholipids, which is oxidised via the lipoxygenase and cyclo-oxgenase pathways to inflammatory metabolites; examples of these include leukotriene $B_4$ ($LTB_4$) and prostaglandin $E_2$ ($PGE_2$). Since human keratinocytes lack the components to produce $LTB_4$, $PGE_2$ is probably the more important inflammatory metabolite in epidermis.

Therefore, these Borignaceae oils (and derivatives thereof) are useful for treating skin inflammation, particularly skin inflammation caused by radiation, such as UV radiation. They are particularly useful in treating bums, particularly first degree burns such as sunburn; they can also be used prophylactically as part of a sunscreen composition. Broadly, the invention may be applied to treat skin irritation caused by over-exposure to a wide variety of radiation, including UV radiation, infrared radiation, and radiation used during chemotherapy.

The oil extract can be used in a wide variety of topical applications, including many cosmetic and dermatological applications. The oil extract itself, or compositions formed from the oil extract, can be used to treat a wide variety of skin disorders, such as dry skin, itchy skin, psoriasis, eczema and the like. For example, the oil extract can be used in skin creams and emulsions, including cleansers, moisturising creams and sunscreens; shampoos; and bath oils.

Accordingly, there is provided a composition for topical application by the human or animal body, comprising an oil extracted from the seeds of the Borignaceae family, or a physiologically acceptable derivative thereof, in combination with a physiologically acceptable carrier therefor. The precise nature of the carrier depends on the use desired for the composition. In addition, the carrier would usually contain other active ingredients, such as moisturiser (e.g. for moisturising cream), a surfactant (e.g. for shampoo) or a UV-blocking/absorbing compound (e.g. for a sun-cream). Some specific examples of suitable carriers are disclosed in the Examples below.

According to one aspect of the invention, there is provided a sunscreen composition comprising an oil according to the invention containing stearidonic acid, or a physiologically acceptable derivative thereof, in combination with a UV blocking and/or UV-absorbing material. The term "sunscreen composition" as used in this specification includes materials that substantially completely block UV radiation and includes materials that only partially block UV radiation It is particularly preferred that the sunscreen composition includes one or more of a moisturiser, an emollient, an emulsifier, a preservative, a dispersant, a viscosity modifier, a herbal extract, a solvent, a chelating agent, an antioxidant, a water-proofing agent, apH adjuster, a perfume, and a protein.

It is particularly preferred that the sunscreen composition includes one or more of titanium dioxide; zinc oxide; benzophenone-3; benzophenone-4; octyl methoxycinnamate (Parsol 1789); 3,3,5-trimethycyclohexyl salicylate; carbomer; hydroxeyethyl cellulose; lanolin alcohols; cetyl phosphate; fatty alcohols; $C_{12}$ to $C_{15}$ alkyl benzoate; cyclomethicone; caprylic/capric triglycerides; mineral oil; glycerin; vitamin E; and isopropyl myristate.

The precise formulation of the sunscreen composition depends on the form required for the composition. Broadly, it may be in the form of a solid or a liquid suitable for topical application. Typically, the composition is provided in the form of a cream, an emulsion or a gel; however, the composition may be provided in other forms, such as a solid stick.

According to another aspect of the invention, we provide a pharmaceutical composition for treating skin inflammation caused by burns, by exposure to sunlight or by exposure to UV radiation, comprising an oil according to the invention containing stearidonic acid or a physiologically acceptable derivative thereof, and a physiologically acceptable carrier.

The carrier will include materials normally present in formulations for treating burns, such as antiseptic compounds, emollients, inorganics, humectants, moisturisers, anti-inflammatory agents, vitamins, preservatives, pH adjusters, proteins, herbal extracts, carriers/solvents, soothing/cooling agents, antioxidants, perfumes, emulsifiers and viscosity modifiers. Specific examples of useful materials include glycerine, triethanolamine stearate, vitamin E, lanolin, zinc oxide, allantoin, calamine, sodium lactate, water, lactic acid, pro-vitamin $B_5$ and menthol.

The formulation of the carrier also depends on the form required for the pharmaceutical composition. Broadly, the pharmaceutical composition may be in the form of a solid or a liquid suitable for topical application. Typically, the pharmaceutical composition is provided in the form of a cream, an emulsion or a gel; however, the pharmaceutical composition may be provided in other forms, such as a solid stick.

The amount of the stearidonic acid (or derivative) in the sunscreen composition or the pharmaceutical composition depends upon the way the composition is to be used. However, the compositions according to the invention typically contain 0.1 to 20 wt % of the stearidonic acid, or derivative, preferably 0.2 to 10 wt %.

According to another aspect of the invention there is provided a composition for oral ingestion to the human or animal body, comprising an oil extracted from the seeds of the Borignaceae family, or a physiologically acceptable derivative thereof, in combination with a physiologically acceptable carrier therefor.

The oil also has a wide range of dietetic uses. For example, the oil can be provided as an additive to existing food products, for instance as an additive to milk or milk-based drinks; it may form be in the form of a dietary supplement, or part of a dietary supplement (e.g. a vitamin-containing supplement), and may be provided in solid form, for example as a tablet, as a soft or hard gelatin capsule, or in liquid form, such as for parenteral use.

The amount of oil in the composition also depends upon the desired use. However, for most applications, an amount of the oil in the range of from 1 wt % and 20 wt % is appropriate.

The compositions according to the invention may be provided in a bottle, a tube or any other suitable packaging. The container for the compositions may be provided with dispensing means for dispensing the composition. Any known form of dispensing means may be used. When the composition is a liquid, it may be desirable to employ a dispensing means that can dispense it in the form of a spray.

We have described above the use of oil extracted from the seeds of the Borignaceae family, and compositions including such oils. This oil contains glycerides of a number of fatty acids, including stearidonic acid. However, it is possible to process the oil extracted from the seeds to to convert it at least partially to the corresponding fatty acids of the triglycerides in the oil. This processing would typically comprise a saponification to step to hydrolyse the triglycerides, an acidification step, and optionally at least one separation step to recover the stearidonic acid and other fatty acids. There may also be a purification step to purify the stearidonic acid so produced. Whilst any physiologically acceptable derivative of stearidonic acid may be used in the present invention, it is preferred that the derivative is an ester of stearidonic acid. More preferably the ester comprises an ester of stearidonic acid with an alcohol, particularly an ester of stearidonic acid with a polyol.

The present invention also includes the use of stearidonic acid formed from an oil extracted from seeds of the Borignaceae family in topical application to or for oral ingestion by, the human or animal body. The stearidonic acid so formed may be used alone for these purposes or, preferably, it is used to form part of a composition for topical application to or oral ingestion by, the human or animal body. The stearidonic acid may be part of a mixture of essential fatty acids formed from an oil extracted from the seed of the Borignaceae family.

According to another aspect of the invention there is provided the use of an oil according to the invention containing stearidonic acid or a physiologically acceptable derivative thereof, in a sunscreen composition.

According to another aspect of the invention there is provided the use of an oil according to the invention containing stearidonic acid or a physiologically acceptable derivative thereof, for the manufacture of a medicament for treating skin inflammation caused by burns.

According to another aspect of the invention there is provided the use of an oil according to the invention containing stearidonic acid or a physiologically acceptable derivative thereof, for the manufacture of a medicament for treating skin inflammation caused by exposure to UV radiation, or by exposure to sunlight.

According to another aspect of the invention there is provided a method treating skin inflammation caused by burns, comprising topically applying an oil according to the invention containing stearidonic acid, or a physiologically acceptable derivative thereof, to an inflamed area.

According to another aspect of the invention there is provided a method of treating skin inflammation cause by exposure to UV radiation or exposure to sunlight, comprising topically applying an oil according to the invention containing stearidonic acid, or aphysiologically acceptable derivative thereof, to an inflamed area.

According to another aspect of the invention there is provided the use of an oil according to the invention containing stearidonic acid or a physiologically acceptable derivative thereof, to inhibit the cyclo-oxygenase pathway.

According to another aspect of the invention there is provided the use of an oil according to the invention containing stearidonic acid or a physiologically acceptable derivative thereof, for the manufacture of a medicament for inhibiting the cyclo-oxygenase pathway.

The following examples illustrate the invention, and it will be appreciated that modifications thereto can be made without departing from the spirit or scope of the invention.

EXAMPLE 1

Preparation of Stearidonic Acid from E. plantagineum 10 kg of the seeds of Echium plantagineum were crushed and the oil was extracted with 15 litres of petroleum ether (b.p. 40–60° C.). The petroleum ether extract was evaporated to yield 1741 g of a golden yellow oil. The oil was converted to the corresponding fatty acid methyl esters and was analysed by gas chromatography. The lipid profile was as follows:

| Fatty Acid | Fatty Acid Content |
| --- | --- |
| 16:0 | 7.2% |
| 18:0 | 4.0% |
| 18:1 | 18.2% |
| 18:2 (LA) | 16.5% |
| 18:3 (GLA) | 11.8% |
| 18:3 (ALA) | 28.9% |
| 18:4 (SA) | 12.2% |
| Other | 1.2% |

EXAMPLE 2

Preparation of Stearidonic Acid from T. zeylanicum 20g of the seeds of Trichodesma zeylanicum seeds were crushed and placed in a Soxhlet extraction thimble. An oil was isolated by refluxing n-hexane around the crushed seed to produce a solution of the oil in n-hexane. The oil was separated from the n-hexane by roto-evaporation; 5g of a green oil was recovered.

An aliquot of the oil was converted to the corresponding fatty acid methyl esters and was analysed by gas chromatography. The lipid profile was as follows:

| Fatty Acid | Fatty Acid Content |
|---|---|
| 16:0 | 9.4% |
| 18:0 | 5.7% |
| 18:1 | 25.5% |
| 18:2 (LA) | 19.0% |
| 18:3 (GLA) | 5.5% |
| 18:3 (ALA) | 26.5% |
| 18:3 (SA) | 5.9% |
| Other | 2.5% |

EXAMPLE 3

Comparison of $PGE_2$-Blocking Effects

Synthetic human skin grown from human fibroplasts has been demonstrated to be useful as a model for assessing phototoxity. This model was used to evaluate the inhibiting action of topically-applied lipids.

Duplicate 9×9 mm Model ZK1301 tissues (obtainable from Advanced Tissue Sciences, La Jolla, Calif., USA) were dosed with 3 microlitres of test oil. Control tissues were untreated. The test oils were: blackcurrant seed oil; borage seed oil (this is a Boragnaceae oil with no stearidonic acid); marine oil; the oil from Example 1; and the oil from Example 2. The tissues were incubated for 24 hours at 37° C. in an atmosphere with 5% $CO_2$ and greater than 90% humidity. Half the tissues were then exposed to 4 $J/cm^2$ UVB radiation using a Dr Honle Solar simulator to stimulate the inflammatory response.

The tissues were then incubated for a further 24 hours. The tissue supernatants were collected and the tissues were evaluated for cell viability by an MTT (3(4,5-dimethyl thiazol-2-yl) 2,5-diphenyl tetrazolin bromide) dye reduction assay, using the Skin MTT Assay Kit ZA0022 (available from Advanced Tissue Sciences, La Jolla, Calif., USA). This protocol is based on a published method (T. Mosmann, J. Immunol. Meth. 65 55 (1983)).

A $PGE_2$ assay was performed in the supernatants. $PGE_2$ is a strongly pro-inflammatory eicosanoid; its release is indicative of membrane perturbation events that activate phospholipase $A_2$ to release arachidonic acid. Arachidonic acid is the precursor to $PGE_2$. The $PGE_2$ assay on the supernatant was carried out using a $PGE_2$ assay kit ZA0050, method number 6-FRD0019/Rev 002 (available from Advanced Tissue Sciences, La Jolla, Calif., USA). This method has been described by E. Granstrom et al in Prostaglandin Thrombox. Res. 5 119 (1978).

The results of the MTT Assay were as follows:

| | Mean MTT Optical Density | |
|---|---|---|
| Test Material | No UVB | UVB |
| Control | 1.52 | 1.25 |
| Blackcurrant seed oil | 2.54 | 1.30 |
| Borage seed oil | 1.63 | 1.39 |
| Marine Oil | 1.45 | 1.27 |
| Oil from Example 1 | 1.47 | 1.36 |
| Oil from Example 2 | 1.53 | 1.4 |

None of these materials produced any notable cytotoxicity or phototoxicity.

The results of the $PGE_2$ assay were as follows:

| | Mean $PGE_2$ Release (pg/ml) | |
|---|---|---|
| Test Material | No UVB | UVB |
| Control | 1300 | 17000 |
| Blackcurrant seed oil | 5100 | 15000 |
| Borage seed oil | 1400 | 16000 |
| Marine Oil | 3100 | 19000 |
| Oil from Example 1 | 2400 | 8100 |
| Oil from Example 2 | 2100 | 9600 |

These results demonstrate that UVB irradiation of control tissue caused a 13-fold increase in release of $PGE_2$. Pre-incubation with the oil from Examples 1 and 2 are much more effective than blackcurrant seed oil. The main difference in the blackcurrant seed oil is that it has much less stearidonic acid than the oils in Examples 1 and 2 (typically blackcurrant seed oil contains 3 to 4 wt % of stearidonic acid).

EXAMPLE 4

Sunscreen Oil

| | wt % |
|---|---|
| Butyl methoxydibenzoyl methane (Parsol 1789)(1) | 2.0 |
| Octyl methoxycinnamate (Parsol MCX)(1) | 7.5 |
| Benzophenone-3 (Uvinul M40)(2) | 4.5 |
| PPG-2 myristyl ether propionate (Promyristyl PM3)(3) | 10.0 |
| Oil from Example 1 | 2.0–10.0 |
| Caprylic/capric trigylcerides (Crodamol GTCC) | to 100 |
| Perfume, preservatives, colour | qs |

(1) From Givaudan
(2) From BASF
(3) From Croda

The sunscreen oil was formed by blending the ingredients, whilst heating gently. The resultant blend was stirred to cool.

EXAMPLE 5

Physical Block Sunscreen Cream

| | wt % |
|---|---|
| Oil Phase: | |
| Myristyl myristate (Crodamol MM)(1) | 1.5 |
| Dimethicone (silicone 200/200)(2) | 7.0 |
| Glyceryl stearate (GMS N/E DP2186)(1) | 2.5 |
| Stearic acid (Crosterene SA4130)(1) | 3.0 |
| PVP/eicosene copolymer (Antaron V220)(3) | 0.5 |
| Non-ionic emulsifying blend (Polawax GP200 DP2307)(1) | 2.0 |
| Octyl hydroxy stearate (Crodamol OHS)(1) | 5.0 |
| Oil from Example 1 | 2.0–10.0 |
| Super-refined shea butter(1) | 5.0 wt % |
| Caprylic/capric trigylcerides (Crodamol GTCC)(1) | 9.0 wt % |
| Titanium dioxide | 5.0 wt % |

-continued

| | wt % |
|---|---|
| Water Phase: | |
| Flobeads (CL-2080)(5) | 5.0 |
| Glycerine | 3.0 |
| Triethanolamine | 0.9 |
| Perfume, preservatives, colour | qs |
| Deionised water | balance |

(1) From Croda
(2) From Dow Corning
(3) From GAF
(4) From K&K Greef
(5) From Landsdowne Chemicals The sunscreen cream was made by heating the oil phase (including titanium dioxide) and water phase separately to 80–85° C., then adding the water phase to the oil phase with vigorous agitation. The triethanolamine was then added. At 45° C. the Flobeads were added. The stirring was continued until the temperature reached about 55° C., and then the composition was passed through suitable homogenising equipment, such as a triple roll mill.

EXAMPLE 6

Antioxidant Cream

| | wt % |
|---|---|
| Oil Phase: | |
| Cosmowax D (cetearyl alcohol (and) Cetearyth 20)(1) | 2.10 |
| Crilket 3 (Polysorbate 60)(1) | 2.50 |
| Crodacol C90 (cetyl alcohol)(1) | 2.50 |
| Crodamol GTCC (capric/caprylic trigylcerides)(1) | 7.50 |
| Vitamin E(2) | 0.50 |
| Ascorbyl palmitate (2) | 0.20 |
| SR Echium Oil (1) | 2.00 |
| Water Phase: | |
| Cellosize QP30000H (hydroxyethyl cellulose)(3) | 0.50 |
| Croderol GA7000 (Glycerin)(1) | 2.00 |
| Deionised water | to 100 |
| Perfume, Preservative, colour | qs |

(1) From Croda
(2) From Roche
(3) From Union Carbide

The oil and water phases were heated separately to 65–70° C., then the water phase was added to the oil phase while stirring. The composition was then stirred to cool.

EXAMPLE 7

Cooling After-sun Cream

| | wt % |
|---|---|
| Oil Phase: | |
| Crodamol IPM (isopropyl stearate)(1) | 5.00 |
| Crodamol CAP (cetearyl octanoate)(1) | 2.00 |
| SR Trichodesma Oil(1) | 2.00 |
| Polawax GP200 (non-ionic emulsifying wax)(1) | 2.00 |
| Cithrol GMS A/S (glyceryl stearate (and) PEG-100 stearate)(1) | 3.00 |

-continued

| | wt % |
|---|---|
| Silicone Fluid 200/100 cs (dimethicone)(2) | 0.50 |
| Menthol | 0.10 |
| Allantoin | 0.25 |
| Water Phase: | |
| Carbopol 934 (Carbomer 934)(3) | 0.25 |
| Ethanol DEB 100 | 2.00 |
| Triethanolainine 99% | to pH 6.5 |
| Deionised water | to 100% |
| Perfume, preservative, colour | qs |

(1) From Croda
(2) From Dow Corning
(3) From B F Goodrich

The carbopol was first hydrated in water at about 60–65° C., then the remaining water-phase ingredients were added. Both phases were then heated to 65–70° C., and then the water phase was added to the oil phase whilst stirring. Finally, the composition was neutralised with the amine and stirred to cool.

EXAMPLE 8

Calamine Cream

| | wt % |
|---|---|
| Oil Phase: | |
| Polawax GP200 (non-ionic emulsifying wax)(1) | 8.00 |
| Crillet 3 (Polysorbate 60)(1) | 1.00 |
| SR Trichodesma oil(1) | 2.00 |
| Crodamol GTCC (capric/caprylic triglycerides)(1) | 3.00 |
| Water Phase: | |
| Distilled Witch Hazel | 10.00 |
| Croderol GA7000(1) | 5.00 |
| Zinc oxide | 2.00 |
| Calamine | 2.00 |
| Deionised water | to 100 |
| Perfume, preservative, colour | qs |

The oil and water phases were heated separately to 65–70° C. The two phases were then combined while stirring. The zinc oxide and calamine was then added under high shear. Finally, the composition was stirred to cool.

EXAMPLE 5

Shampoo

| | wt % |
|---|---|
| Sodium laureth sulphate (Empicol ESB3)(1) | 50.0 |
| Cocamidopropyl betaine (Incronam 30)(2) | 5.0 |
| Oil from Example 1 | 1 to 5 |
| Polysorbate 20 (Crillet 1)(2) | 3.0 |
| PPG-5-ceteth-10-phosphate (Crodafos SG)(2) | 3.0 |
| Triethanolamine | to pH 6.5–7.0 |
| Butylated hydroxytoluene | 0.01 |

-continued

| | wt % |
|---|---|
| De-ionised water | balance |
| Perfume, preservatives, colour | qs |

(1) From Albright & Wilson
(2) From Croda

The shampoo was prepared by first forming a pre-mix by solubilising the essential fatty acid-containing oil from Example 1 in the surfactant mixture (Polysorbate 20 and PPG-5-ceteth-10-phosphate). The other ingredients were combined and, when homogeneous, were added to the pre-mix. The resultant mixture was stirred until clear.

EXAMPLE 6

Cleanser

| | wt % |
|---|---|
| Oil Phase: | |
| Non-ionic emulsifying wax (Polawax GP200)(1) | 2.0 |
| Cetearyl alcohol (Crodacol CS90EP)(1) | 1.0 |
| Glyceryl stearate (Cithrol GMS N/E DP2186)(1) | 1.0 |
| Caprylic/capric triglycerides (Crodamol GTCC)(1) | 8.0 |
| Rosehip oil (2) | 1.0 |
| Oil from Example 1 | 1 to 10 |
| Water Phase: | |
| Glycerin | 2.0 |
| Carbomer 981 (Carbopol 981 - 2% aqueous solution)(3) | 5.0 |
| Triethanolamine | to pH 6.5 |
| De-ionised water | balance |
| Perfume, preservative, colour | qs |

(1) From Croda
(2) From Novarom
(3) From B F Goodrich

The cleanser was prepared by heating the water and oil phases separately to 65–70° C., then adding the water phase to the oil phase with stirring. The pH was then adjusted to pH 6.5 with the triethanolamine. The resultant mixture was stirred to cool.

EXAMPLE 7

Moisturising Facial Oil

| | wt % |
|---|---|
| Oil from Example 1 | 5.0 to 15.0 |
| Tocopheryl actetate(2) | 5.0 |
| Butylated hydroxytoluene | 0.05 |
| Caprylic/capric triglycerides (Crodamol GTCC)(1) | balance |
| Perfume, preservatives, colour | qs |

(1) From Croda
(2) From Roche

The facial oil was prepared by incorporating the butylated hydroxytoluene in the caprylic/capric triglycerides with gentle warming and stirring. The resultant mixture was stirred to cool, then the remaining ingredients were added whilst continuing stirring.

EXAMPLE 8

Moisturising Body Cocktail

| | wt % |
|---|---|
| Oil from Example 1 | 5.0 to 20.0 |
| Super-refined grapeseed oil(1) | 20.0 |
| Tocopheryl acetate(2) | 2.0 |
| Caprylic/capric triglycerides (Crodamol GTCC)(1) | balance |
| Perfume, preservative, colour | qs |

(1) From Croda
(2) From Roche

The body cocktail was prepared by combining the preservatives and the capcylic/capric triglycerides with gentle warming and stirring. The resultant mixture was stirred to cool. The remaining ingredients were added, whilst continuing stirring.

EXAMPLE 9

Dispersible Bath Oil

| | wt % |
|---|---|
| Oil from Example 1 | 1.0 to 5.0 |
| Toeopheryl acetate(2) | 3.0 to 5.0 |
| Laureth-3 (Volpo L3 Special)(1) | 12.5 |
| Isopropyl myristate (Crodamol IPM)(1) | 20.0 |
| Caprylic/capric triglycerides (Crodaniol GTCC)(1) | balance |
| Perfume, preservatives, colour | qs |

(1) From Croda
(2) From Roche

The bath oil was prepared by adding the preservatives to the caprylic/capric triglycerides with gentle warming and stirring. The remaining ingredients were added, and the resultant mixture was stirred to cool.

EXAMPLE 10

Skin Lotion

| | wt % |
|---|---|
| Oil Phase: | |
| Oil from Example 2 | 5.0 to 10.0 |
| $C_{10}$–$C_{30}$ cholesterol/lanosterol esters (Super Sterol ester)(1) | 1.0 |
| Stearic acid (Crosterene SA4130)(1) | 2.0 |
| Glyceryl stearate S/E (GMS S/E GE0802)(1) | 2.0 |
| Non-onic emulsifying wax (Polawax GP200)(1) | 0.75 |
| Water Phase: | |
| Glycerin | 6.0 |
| Triethanolamine | 0.9 |
| De-ionised water | balance |
| Perfume, preservatives, colour | qs |

(1) From Croda

The skin lotion was prepared by heating the oil and water phases separately to 65–70° C., then adding the water phase to the oil phase while stirring. The resultant mixture was stirred to cool, and the perfume was added at 45° C.

EXAMPLE 11

Emollient Skin Cream

| | wt % |
|---|---|
| Oil Phase: | |
| Oil from Example 2 | 10 |
| Non-ionic emulsifying wax (Polawax GP200(1) | 4.0 |
| Synthetic beeswax (Syncrowax BB4)(1) | 2.0 |
| Myristyl myristate (Crodamol MM)(1) | 1.0 |
| Butylated hydroxytoluene | 0.05 |
| Water Phase: | |
| Carbomer 941 (Carbopol 941)(2) | 0.2 |
| Triethanolamine | 0.2 |
| De-ionised water | balance |
| Perfume, preservatives colour | qs |

(1) From Croda
(2) From B F Goodrich

The skin cream was prepared by hydrating the Carbopol 941 in water at 60–70° C., then adding the rest of the aqueous phase components at a similar temperature while stirring. The oil phase components were heated to 65–70° C., then the water phase components were added to the oil phase components at 65° C., whilst stirring. The perfume was added when the cream had cooled to below 45° C.

EXAMPLE 12

Emollient Skin Cream

| | wt % |
|---|---|
| Oil Phase: | |
| Oil from Example 2 | 20 |
| Non-ionic emulsifying wax (Polawax GP200))(1) | 5.0 |
| Synthetic beeswax (Syncrowax BB4)(1) | 2.0 |
| Cetostearyl stearate (Crodamol CSS)(1) | 5.0 |
| Butylated hydroxytoluene | 0.05 |
| Water Phase: | |
| Carbomer 941 (Carbopol 941)(2) | 0.2 |
| Triethanolamine | 0.2 |
| Glycerin | 3.0 |
| De-ionised water | balance |
| Perfume, preservatives, colour | qs |

(1) From Croda
(2) From B F Goodrich

The skin cream was prepared by hydrating the Carbopol 941 in water at 60–70° C., then adding the rest of the aqueous phase components at a similar temperature while stirring. The oil phase components were heated to 65–70° C., then the water phase components were added to the oil phase components at 65° C. whilst stirring. The perfume was added when the cream had cooled to below 45° C.

EXAMPLE 13

Emollient Dispersible Bath Oil

| | wt % |
|---|---|
| PEG-20 Evening Primrose glycerides (Crovol EP40(1) | 15.0 |
| Oleyl alcohol (Novol)(1) | 17.5 |
| Octyl palmitate (Crodamol OP)(1) | 8.0 |
| Oil from Example 2 | 1.0 to 20.0 |
| Light mineral oil (25cS/25° C.) | balance |
| Perfume, preservatives, colour | qs |

(1) From Croda

The bath oil was prepared by blending all the ingredients together at ambient temperature.

EXAMPLE 14

Dietetic Emulsion

| | wt % |
|---|---|
| Oil from Example 1 | 10.0 |
| Lecithin (Centomix E)(1) | 2.0 |
| Sorbitan monolaureate (Crill 1)(2) | 1.66 |
| Polysorbate 20 (Crillet 1)(2) | 0.34 |
| Distilled water | 86 |

(1) From Stern
(2) From Croda

The emulsion was prepared by adding the emulsifiers to the oil, then adding the water while homogenising the mixture for 5 minutes. The resultant emulsion can be used for human ingestion as a dietary supplement. It can be used as an additive for milk or milk drinks.

EXAMPLE 15

Dietetic Emulsion

| | wt % |
|---|---|
| Oil from Example 2 | 10.0 |
| Sorbitan monolaureate (Crill 1)(1) | 1.66 |
| Polysorbate 20 (Crillet 1)(1) | 0.34 |
| Distilled water | 88 |

(1) From Croda

The emulsion was prepared by adding the emulsifiers to the oil, then adding the water while homogenising the mixture for 5 minutes. The resultant emulsion can be used for human ingestion as a dietary supplement. It can be used as an additive for milk or milk drinks.

We claim:

1. A composition comprising in the range of from 1 to 20% by weight of the total composition of an oil extracted from the seeds of Boraginaceae, which oil comprises in the range of from 5 to 20% stearidonic acid triglyceride and 80 to 95% of other fatty acid triglycerides, by weight of the total fatty acids in the oil extract, which stearidonic acid triglyceride or other fatty acid triglyceride(s) may optionally have been converted to an ester thereof, and optionally a physiologically acceptable carrier therefor.

2. A composition according to claim 1, wherein the oil is an extract from seeds of the group consisting of Echium and Trichodesma species.

3. A composition according to claim 1, wherein the oil is an extract from seeds of the group consisting of Echium species.

4. A composition according to claim 1, in a form suitable for dietetic use.

5. A composition according to claim 1, wherein the oil is added to food products.

6. A composition according to claim 1, wherein the oil is in the form of a dietary supplement.

7. A composition according to claim 1, in a form suitable for cosmetic use.

8. A composition according to claim 1, in a form suitable for healthcare or pharmaceutical use.

9. A composition according to claim 1, in solid form.

10. A composition according to claim 1, in liquid form.

11. A composition according to claim 1, whereby the oil provides greater inhibition of $PGE_2$ release than borage seed oil.

12. A composition according to claim 1, wherein the oil comprises at least 10 wt % of the triglyceride of stearidonic acid.

13. A composition according to claim 1, wherein the derivative is the corresponding fatty acid ester.

14. A composition according to claim 1, wherein the oil comprises at least 12.2 wt % of the methyl ester of stearidonic acid.

15. A composition according to claim 1, wherein the oil is an extract from seeds of *Echium plantagineum*.

16. A composition according to claim 15, in a form suitable for dietetic use.

17. A composition according to claim 15, wherein the oil is added to food products.

18. A composition according to claim 15, wherein the oil is in the form of a dietary supplement.

19. A composition according to or claim 15, in a form suitable for cosmetic use.

20. A composition according to claim 15, in a form suitable for healthcare or pharmaceutical use.

21. A composition according to or claim 15, in solid form.

22. A composition according to claim 15, in liquid form.

23. A composition according to claim 15, whereby the oil provides greater inhibition of PGE2 release than borage seed oil.

24. A composition according to claim 15, wherein the oil comprises at least 10 wt % of the triglyceride of stearidonic acid.

25. A composition according to claim 15, wherein the stearidonic and other fatty acids are in the form of the corresponding fatty acid ester.

26. A composition according to claim 15, wherein the oil comprises at least 12.2 wt % of the methyl ester of stearidonic acid.

27. A method for supplementing stearidonic acid in a human or animal body, which method comprises administration to a patient in need thereof a composition according to claim 1.

28. A method for supplementing stearidonic acid in a human or animal body, which method comprises administration to a patient in need thereof of a composition according to claim 16.

29. A composition comprising in the range of from 1 to 20% by weight of the total composition of an extract of an oil extracted from the seeds of Boraginaceae comprising in the range of from 5 to 20% stearidonic acid triglyceride and 80 to 95% of other fatty acid triglycerides selected from the triglycerides of 16:0, 18:0, 18:1, 18-.2 (LA), 18:3 (GLA), 18:3 (ALA) and minor amounts of other fatty acid triglycerides, by weight of the total fatty acids in the oil extract, which stearidonic acid or other fatty acid(s) may optionally have been converted to an ester thereof, and optionally a physiologically acceptable carrier therefor, whereby the oil is provides greater inhibition of $PGE_2$ release than borage seed oil.

30. A method for supplementing stearidonic acid in a human or animal body, which method comprises administration to a patient in need thereof of a composition according to claim 29.

31. A composition according to claim 29, wherein the oil is an extract from *Echium plantagineum*.

32. A method for supplementing stearidonic acid in a human or animal body, which method comprises administration to a patient in need thereof of a composition according to claim 31.

* * * * *